US008328874B2

(12) United States Patent
Lee

(10) Patent No.: US 8,328,874 B2
(45) Date of Patent: *Dec. 11, 2012

(54) MOBILE BEARING ASSEMBLY

(75) Inventor: Jordan S. Lee, Warsaw, IN (US)

(73) Assignee: DePuy Products, Inc., Warsaw, IN (US)

( * ) Notice: Subject to any disclaimer, the term of this patent is extended or adjusted under 35 U.S.C. 154(b) by 230 days.

This patent is subject to a terminal disclaimer.

(21) Appl. No.: 12/049,753

(22) Filed: Mar. 17, 2008

(65) Prior Publication Data

US 2008/0243262 A1    Oct. 2, 2008

Related U.S. Application Data

(60) Provisional application No. 60/909,127, filed on Mar. 30, 2007.

(51) Int. Cl.
*A61F 2/38*    (2006.01)

(52) U.S. Cl. .................. 623/20.3; 623/20.33; 623/20.15

(58) Field of Classification Search ...... 623/20.3–20.32, 623/20.21, 20.34, 20.33, 20.13–20.15, 20.22, 623/20.28–20.29, 21.17–21.18, 20.26

See application file for complete search history.

(56) References Cited

U.S. PATENT DOCUMENTS

| | | | |
|---|---|---|---|
| 3,506,982 A | 4/1970 | Steffee | |
| 3,605,123 A | 9/1971 | Hahn | |
| 3,855,638 A | 12/1974 | Pilliar | |
| 3,906,550 A | 9/1975 | Rostoker et al. | |
| 3,953,899 A | 5/1976 | Charnley | |
| 4,016,606 A | 4/1977 | Murray et al. | |
| 4,205,400 A | 6/1980 | Shen et al. | |
| 4,207,627 A | 6/1980 | Cloutier | |
| 4,213,816 A | 7/1980 | Morris | |
| 4,216,549 A | 8/1980 | Hillberry et al. | |
| 4,224,696 A | 9/1980 | Murray et al. | |
| 4,224,697 A | 9/1980 | Murray et al. | |
| 4,340,978 A | 7/1982 | Buechel et al. | |
| 4,454,612 A | 6/1984 | McDaniel et al. | |
| 4,470,158 A | 9/1984 | Pappas et al. | |

(Continued)

FOREIGN PATENT DOCUMENTS

BE    1008201    2/1996

(Continued)

OTHER PUBLICATIONS

"The Oxford Partial Knee", Biomet Patients and Caregivers—Joint Replacement, www.biomet.com/patients/oxford.cfm, Biomet, Inc. 2008, 3 pages.

(Continued)

*Primary Examiner* — William H. Matthews
*Assistant Examiner* — Marcia Hoffman
(74) *Attorney, Agent, or Firm* — Barnes & Thornburg LLP

(57) ABSTRACT

A mobile tibial assembly includes a tibial tray and a unicompartmental tibial insert configured to move relative to the tibial tray. The tibial insert includes a platform having an upper bearing surface and a stem extending downwardly from a bottom surface of the unicompartmental insert. The tibial tray includes a corresponding recess, such as a cavity and/or a channel, configured to receive the stem therein such that the stem and the recess cooperate to constrain the movement of the unicompartmental tibial insert relative to the tibial tray. The stem of the unicompartmental tibial insert is configured to extend below the bottom surface of the tibial tray when received in the cavity.

12 Claims, 4 Drawing Sheets

U.S. PATENT DOCUMENTS

| | | | | |
|---|---|---|---|---|
| 4,479,271 A | | 10/1984 | Bolesky | |
| 4,501,031 A | | 2/1985 | McDaniel et al. | |
| 4,568,348 A | | 2/1986 | Johnson et al. | |
| 4,589,883 A | | 5/1986 | Kenna | |
| 4,636,219 A | | 1/1987 | Pratt et al. | |
| 4,718,413 A | | 1/1988 | Johnson | |
| 4,719,908 A | | 1/1988 | Averill et al. | |
| 4,728,332 A | | 3/1988 | Albrektsson | |
| 4,743,261 A | * | 5/1988 | Epinette | 623/20.32 |
| 4,795,468 A | | 1/1989 | Hodorek et al. | |
| 4,911,721 A | | 3/1990 | Branemark et al. | |
| 4,936,847 A | | 6/1990 | Manginelli | |
| 4,944,757 A | | 7/1990 | Martinez et al. | |
| 4,950,298 A | | 8/1990 | Gustilo et al. | |
| 4,997,445 A | | 3/1991 | Hodorek | |
| 5,019,103 A | | 5/1991 | Van Zile et al. | |
| 5,047,058 A | | 9/1991 | Roberts et al. | |
| 5,108,452 A | | 4/1992 | DeMane et al. | |
| 5,152,797 A | | 10/1992 | Luckman et al. | |
| 5,201,769 A | | 4/1993 | Schutzer | |
| 5,226,915 A | | 7/1993 | Bertin | |
| 5,263,987 A | | 11/1993 | Shah | |
| 5,282,868 A | | 2/1994 | Bahler | |
| 5,330,532 A | | 7/1994 | Ranawat | |
| D354,810 S | | 1/1995 | Nazre | |
| 5,395,401 A | | 3/1995 | Bahler | |
| D357,534 S | | 4/1995 | Hayes | |
| D359,557 S | | 6/1995 | Hayes | |
| 5,458,637 A | | 10/1995 | Hayes | |
| 5,609,639 A | * | 3/1997 | Walker | 623/20.29 |
| 5,609,640 A | | 3/1997 | Johnson | |
| 5,658,341 A | | 8/1997 | Delfosse | |
| 5,702,458 A | | 12/1997 | Burstein et al. | |
| 5,702,459 A | | 12/1997 | Hummer et al. | |
| 5,716,361 A | | 2/1998 | Masini | |
| 5,755,801 A | | 5/1998 | Walker et al. | |
| 5,800,560 A | | 9/1998 | Draenert | |
| 5,810,827 A | | 9/1998 | Haines et al. | |
| 5,824,106 A | * | 10/1998 | Fournol | 623/21.18 |
| 5,855,296 A | | 1/1999 | McCann et al. | |
| 5,871,541 A | | 2/1999 | Gerber | |
| 5,879,354 A | | 3/1999 | Haines et al. | |
| 5,888,034 A | | 3/1999 | Greenberg | |
| 5,944,722 A | | 8/1999 | Masini | |
| 5,947,973 A | | 9/1999 | Masini | |
| 5,957,926 A | | 9/1999 | Masini | |
| 5,957,979 A | * | 9/1999 | Beckman et al. | 623/20.33 |
| 5,961,523 A | | 10/1999 | Masini | |
| 5,971,989 A | | 10/1999 | Masini | |
| 6,004,351 A | | 12/1999 | Tomita et al. | |
| 6,010,534 A | | 1/2000 | O'Neil et al. | |
| 6,019,767 A | | 2/2000 | Howell | |
| 6,039,764 A | | 3/2000 | Pottenger et al. | |
| 6,056,754 A | | 5/2000 | Haines et al. | |
| 6,068,633 A | | 5/2000 | Masini | |
| 6,077,269 A | | 6/2000 | Masini | |
| 6,102,916 A | | 8/2000 | Masini | |
| 6,106,529 A | | 8/2000 | Techiera | |
| 6,123,728 A | | 9/2000 | Brosnahan et al. | |
| 6,139,581 A | | 10/2000 | Engh et al. | |
| 6,171,340 B1 | | 1/2001 | McDowell | |
| 6,187,010 B1 | | 2/2001 | Masini | |
| 6,197,064 B1 | | 3/2001 | Haines et al. | |
| 6,214,011 B1 | | 4/2001 | Masini | |
| 6,254,604 B1 | | 7/2001 | Howell | |
| 6,254,605 B1 | | 7/2001 | Howell | |
| 6,296,666 B1 | | 10/2001 | Gardner | |
| 6,361,564 B1 | | 3/2002 | Marceaux et al. | |
| 6,419,707 B1 | * | 7/2002 | Leclercq | 623/20.33 |
| 6,428,577 B1 | | 8/2002 | Evans et al. | |
| 6,494,914 B2 | | 12/2002 | Brown et al. | |
| 6,503,254 B2 | | 1/2003 | Masini | |
| 6,506,215 B1 | * | 1/2003 | Letot et al. | 623/20.29 |
| 6,520,964 B2 | | 2/2003 | Tallarida et al. | |
| 6,602,292 B2 | | 8/2003 | Burkinshaw | |
| 6,616,696 B1 | | 9/2003 | Merchant | |
| 6,660,039 B1 | | 12/2003 | Evans et al. | |
| 6,702,821 B2 | | 3/2004 | Bonutti | |
| 6,730,128 B2 | | 5/2004 | Burstein | |
| 6,770,078 B2 | | 8/2004 | Bonutti | |
| 6,869,448 B2 | | 3/2005 | Tuke et al. | |
| 6,916,341 B2 | | 7/2005 | Rolston | |
| 6,946,001 B2 | | 9/2005 | Sanford et al. | |
| 7,033,397 B2 | | 4/2006 | Webster et al. | |
| 7,101,401 B2 | | 9/2006 | Brack | |
| 7,105,027 B2 | | 9/2006 | Lipman et al. | |
| 7,115,131 B2 | | 10/2006 | Engh et al. | |
| 7,708,741 B1 | | 5/2010 | Bonutti | |
| 7,931,690 B1 | * | 4/2011 | Bonutti | 623/18.11 |
| 2001/0037155 A1 | | 11/2001 | Merchant | |
| 2002/0055784 A1 | | 5/2002 | Burstein et al. | |
| 2003/0009232 A1 | | 1/2003 | Metzger et al. | |
| 2003/0028196 A1 | | 2/2003 | Bonutti | |
| 2003/0033018 A1 | | 2/2003 | Merchant | |
| 2003/0120346 A1 | | 6/2003 | Mercinek et al. | |
| 2003/0158606 A1 | | 8/2003 | Coon et al. | |
| 2003/0181984 A1 | | 9/2003 | Abendschein | |
| 2003/0187510 A1 | | 10/2003 | Hyde | |
| 2003/0195633 A1 | | 10/2003 | Hyde | |
| 2004/0006394 A1 | * | 1/2004 | Lipman et al. | 623/20.29 |
| 2004/0039447 A1 | | 2/2004 | Simon et al. | |
| 2004/0107000 A1 | | 6/2004 | Felt et al. | |
| 2004/0143338 A1 | | 7/2004 | Burkinshaw et al. | |
| 2004/0153066 A1 | | 8/2004 | Coon et al. | |
| 2004/0153164 A1 | | 8/2004 | Sanford et al. | |
| 2004/0167630 A1 | | 8/2004 | Rolston | |
| 2004/0193280 A1 | | 9/2004 | Webster et al. | |
| 2004/0254645 A1 | | 12/2004 | Arnin et al. | |
| 2005/0015153 A1 | | 1/2005 | Goble et al. | |
| 2005/0027365 A1 | * | 2/2005 | Burstein et al. | 623/20.32 |
| 2005/0096747 A1 | | 5/2005 | Tuttle et al. | |
| 2005/0119663 A1 | | 6/2005 | Keyer et al. | |
| 2005/0119664 A1 | | 6/2005 | Carignan et al. | |
| 2005/0143830 A1 | | 6/2005 | Marcinek et al. | |
| 2005/0143831 A1 | | 6/2005 | Justin et al. | |
| 2005/0143833 A1 | | 6/2005 | Merchant | |
| 2005/0149041 A1 | | 7/2005 | McGinley et al. | |
| 2005/0171604 A1 | | 8/2005 | Michalow | |
| 2005/0171612 A1 | | 8/2005 | Rolston | |
| 2005/0177242 A1 | | 8/2005 | Lotke | |
| 2005/0197709 A1 | | 9/2005 | Schaefer et al. | |
| 2005/0203384 A1 | | 9/2005 | Sati et al. | |
| 2005/0234465 A1 | | 10/2005 | McCombs et al. | |
| 2005/0240273 A1 | | 10/2005 | Khandkar et al. | |
| 2005/0278034 A1 | | 12/2005 | Johnson et al. | |
| 2006/0004460 A1 | | 1/2006 | Engh et al. | |
| 2006/0009776 A1 | | 1/2006 | Justin et al. | |
| 2006/0009854 A1 | | 1/2006 | Justin et al. | |
| 2006/0009855 A1 | | 1/2006 | Goble et al. | |
| 2006/0030855 A1 | | 2/2006 | Haines | |
| 2006/0030945 A1 | | 2/2006 | Wright | |
| 2006/0085072 A1 | | 4/2006 | Funk et al. | |
| 2006/0089720 A1 | | 4/2006 | Schneier | |
| 2006/0122616 A1 | | 6/2006 | Bennett et al. | |
| 2006/0129246 A1 | | 6/2006 | Steffensmeier | |
| 2006/0190086 A1 | * | 8/2006 | Clemow et al. | 623/20.15 |
| 2006/0195195 A1 | | 8/2006 | Burstein et al. | |
| 2006/0195196 A1 | | 8/2006 | Pendleton et al. | |
| 2006/0235537 A1 | * | 10/2006 | Kuczynski et al. | 623/20.3 |
| 2006/0265079 A1 | | 11/2006 | D'Alessio | |
| 2007/0010890 A1 | | 1/2007 | Collazo | |
| 2007/0100459 A1 | | 5/2007 | Rhodes | |
| 2007/0100460 A1 | | 5/2007 | Rhodes | |
| 2008/0033567 A1 | | 2/2008 | Stchur | |
| 2008/0086210 A1 | | 4/2008 | Fox | |

FOREIGN PATENT DOCUMENTS

| | | |
|---|---|---|
| DE | 10012060 | 9/2001 |
| DE | 10053623 | 5/2002 |
| EP | 0135319 A2 | 3/1985 |
| EP | 0183670 | 6/1986 |
| EP | 0327387 A2 | 8/1989 |
| EP | 0328463 A1 | 8/1989 |
| EP | 0874596 A1 | 11/1998 |
| EP | 0709075 B1 | 8/2001 |
| EP | 1327424 | 7/2003 |
| EP | 1329205 A1 | 7/2003 |

| | | | | | | |
|---|---|---|---|---|---|---|
| EP | 1374782 | A2 | 1/2004 | WO | 2006074503 A1 | 7/2006 |
| EP | 1442726 | | 8/2004 | WO | 2006078511 A1 | 7/2006 |
| EP | 1442728 | A2 | 8/2004 | WO | 2006078528 A2 | 7/2006 |
| EP | 1550418 | | 7/2005 | WO | 2006078864 A1 | 7/2006 |
| EP | 1557144 | A1 | 7/2005 | WO | 2006106419 A2 | 10/2006 |
| EP | 1584309 | | 10/2005 | WO | 2006112911 A2 | 10/2006 |
| EP | 1669034 | A1 | 6/2006 | | | |
| EP | 1702590 | A2 | 9/2006 | | | |
| EP | 1741412 | | 1/2007 | | | |
| FR | 2663536 | | 12/1991 | | | |
| FR | 2702369 | | 9/1994 | | | |
| FR | 2721820 | | 1/1996 | | | |
| FR | 2885516 | | 11/2006 | | | |
| GB | 2355935 | | 5/2001 | | | |
| JP | 2002272756 | | 9/2002 | | | |
| WO | 9110412 | A1 | 7/1991 | | | |
| WO | 9524874 | | 9/1995 | | | |
| WO | 9716129 | A1 | 5/1997 | | | |
| WO | 0013616 | A1 | 3/2000 | | | |
| WO | 0170143 | A1 | 9/2001 | | | |
| WO | 0209623 | | 2/2002 | | | |
| WO | 03068119 | A2 | 8/2003 | | | |
| WO | 04001569 | A1 | 12/2003 | | | |
| WO | 2005009298 | A1 | 2/2005 | | | |
| WO | 2005025451 | A2 | 3/2005 | | | |
| WO | 2005037065 | A2 | 4/2005 | | | |
| WO | 2005044150 | A1 | 5/2005 | | | |
| WO | 2005069957 | A2 | 8/2005 | | | |

OTHER PUBLICATIONS

"Preservation Uni-compartmental Knee", DePuy Orthopaedics, Inc. 2002, 31 pages.

European Search Report for European Patent Application No. 08251213.8-2310, Jul. 9, 2008, 7 pgs.

Extended European Search Report for European Patent Application No. 10189881.5-2310, Feb. 17, 2011, 6 pgs.

Extended European Search Report for European Patent Application No. 10189885.6-2310, Mar. 18, 2011, 7 pages.

European Search Report for European Patent Application No. 08251210.4-2310, Jun. 20, 2008, 7 pgs.

European Search Report for European Patent Application No. 08251211.2-2310, Jul. 21, 2008, 7 pgs.

European Search Report for European Patent Application No. 08251209.6-2310, Jul. 9, 2008, 7 pgs.

European Search Report for European Patent Application No. 08251212.0-2310, Jul. 21, 2008, 7 pgs.

* cited by examiner

MOBILE BEARING ASSEMBLY

This patent application claims priority to and the benefit of U.S. Provisional Patent Application Ser. No. 60/909,127 entitled "Mobile Bearing Assembly" by Jordan S. Lee, which was filed on Mar. 30, 2007, the entirety of which is expressly incorporated herein by reference.

CROSS-REFERENCE TO RELATED APPLICATIONS

Cross-reference is made to U.S. Utility patent application Ser. No. 11/694,389 entitled "MOBILE BEARING ASSEMBLY HAVING OFFSET DWELL POINT," which was filed on Mar. 30, 2007 by Jordan S. Lee et al. (265280-201238), to U.S. Utility patent application Ser. No. 12/049,750 entitled "MOBILE BEARING ASSEMBLY HAVING A CLOSED TRACK," which was filed on Mar. 17, 2008 by Joseph G. Wyss et al. (265280-204351), to U.S. Utility patent application Ser. No. 12/049,759 entitled "MOBILE BEARING ASSEMBLY HAVING MULTIPLE ARTICULATION INTERFACES," which was filed on Mar. 17, 2008 by Jordan S. Lee et al. (265280-204352), and to U.S. Utility patent application Ser. No. 12/049,699 entitled "MOBILE BEARING ASSEMBLY HAVING A NON-PLANAR INTERFACE SURFACE," which was filed on Mar. 17, 2008 by Jordan S. Lee et al. (265280-204348), the entirety of all of which is expressly incorporated herein by reference.

TECHNICAL FIELD

The present disclosure relates generally to orthopaedic prostheses, and particularly to tibial assemblies including a tibial tray and a tibial insert.

BACKGROUND

During the lifetime of a patient, it may be necessary to perform a joint replacement procedure on the patient as a result of, for example, disease or trauma. For example, many knee replacement surgeries are performed each year. Total knee replacement or arthroplasty may involve replacement of the mid-shaft portion of the femur, proximal, distal, and/or total femur, and proximal tibia. Unicompartmental knee replacement or arthroplasty involves unicondylar resurfacing. Unicompartmental knee arthroplasty provides an alternative to total knee arthroplasty for rehabilitating knees when only one condyle has been damaged as a result of trauma or disease such as noninflammatory degenerate joint disease or its composite diagnosis of osteoarthritis or post-traumatic arthritis, for example. As such, unicompartmental knee arthroplasty may be indicated for use in patients undergoing surgery for a severely painful and/or disabled joint damaged as a result of osteoarthritis, traumatic arthritis, rheumatoid arthritis, or a failed previous implant when only one condyle of the knee (medial or lateral) is affected. Further, unicompartmental knee replacements may be "multi-piece" replacements in which a separate unicompartmental tibial insert is used to replace each of the medial and lateral condyles of the patient. A single, total femoral component or two partial femoral components may be used to cooperate with the two unicompartment inserts.

In addition, in some knee replacement procedures, a total knee tibial tray may used with a unicompartmental tibial insert. For example, a total knee tibial tray may be used with a single unicompartmental tibial insert to replace either the medial or lateral condyle of the patient's knee. Alternatively, a total knee tibial tray may be used with two unicompartmental tibial inserts, each replacing one of the medial and lateral condyles of the patient's knee. In such applications, the medial and lateral unicompartmental tibial inserts may have different characteristics and be selected based on the orthopaedic considerations associated with the respective condyle of the patient's knee.

Unicompartmental knee replacements are intended to provide increased patient mobility and reduce pain by replacing the damaged knee joint articulation in patients where there is evidence of sufficient sound bone to seat and support the components. Age and activity level factor into all reconstructive procedures and the state of the arthritis determines the treatment. With the advancement of minimally invasive techniques that support unicompartmental knee reconstruction, a growing number of patients are offered this alternative for relief from the disabling pain of arthritis and for the potential benefits of a rapid recovery.

The tibial assembly of a unicompartmental knee prosthesis typically includes a tibial tray configured to be coupled to the patient's tibia and a polymer tibial insert positioned on the tibial tray. As discussed above, the tibial tray may be a total or unicompartmental tibial tray. The tibial insert includes an upper bearing surface configured to engage a corresponding articulating condylar surface of a femoral component coupled to the patient's femur. A mobile tibial assembly generally refers to a tibial assembly in which the tibial insert is movable relative to the tibial tray. In other words, the tibial insert may rotate relative to the tray and/or the tibial insert may move medially, laterally, anteriorly, and/or posteriorly relative to the tibial tray. This motion of the tibial insert relative to the tray may be constrained in any number of ways in order to limit the type of motion of the tibial insert. For example, the tibial insert may be limited to anterior/posterior motion relative to the tibial tray and/or rotation of the tibial insert may be limited to something less than 360 degrees of rotation. A fixed tibial assembly generally refers to a tibial assembly in which the tibial insert is not movable relative to the tibial tray and generally remains in a fixed location thereon. Surgeons may choose between fixed and mobile tibial assemblies depending upon the particular needs of the patient.

Typical mobile tibial assemblies fall into one of two classifications with respect to the insert-to-tray interface: unconstrained and constrained. In an unconstrained mobile tibial assembly, the tibial insert is free to move in all directions relative to the tibial tray. In a constrained mobile tibial assembly, the tibial insert is typically restricted from movement relative to the tibial tray in all but one or more directions and/or movements (e.g., translations and/or rotations).

SUMMARY

According to one aspect of the present disclosure, a mobile tibial assembly includes a tibial tray configured to be coupled to a surgically-prepared surface of the proximal end of a tibia and a unicompartmental tibial insert configured to rest on the tray. The tibial tray includes (i) a platform having an upper surface, (ii) an anchor extending downwardly from a bottom surface of the platform, and (iii) a cavity extending from the upper surface of the platform into the anchor. The tibial insert includes a platform and a stem extending downwardly from the platform and received within the cavity of the tibial tray such that a bottom surface of the stem of the tibial insert is position below a bottom surface of the platform of tibial insert. The platform of the tibial insert includes an upper bearing surface configured to receive the corresponding articulating surface of a single condyle thereon.

Illustratively, the anchor of the tibial tray may include a medial wall, a lateral wall, an anterior wall, a posterior wall, and a bottom wall. The medial, lateral, anterior, and posterior walls may each extend downwardly from the bottom surface of the platform of the tibial tray and may each be angled toward each other in a direction away from the bottom surface of the tibial tray.

Further illustratively, the cavity of the tibial tray may define a generally wedge-shaped opening formed in the upper surface of the platform of the tibial tray. One end of the wedge-shaped opening may be narrower than the other end of the wedge-shaped opening.

Alternatively, the cavity of the tibial tray may define a generally oval-shaped or rectangular-shaped opening formed in the upper surface of the platform of the unicompartmental tibial tray.

In some illustrative embodiments, the width of one end of the opening of the cavity of the tibial tray may be greater than the width of a corresponding end of the stem of the tibial insert. Furthermore, the length of one end of the cavity of the tibial tray may be greater than the length of a corresponding end of the stem of the tibial insert.

Illustratively, the longitudinal axis of the cavity of the tibial tray may be parallel to an inboard surface of the platform of the tibial tray. Alternatively, the longitudinal axis of the cavity may be angled with respect to the inboard surface of the platform of the tibial tray.

In other illustrative embodiments, a bottom surface of the cavity of the tibial tray may be positioned below the bottom surface of the platform of the tibial tray.

According to another aspect, a mobile tibial assembly may include a tibial tray and a unicompartmental tibial insert. The tibial tray may be configured to be coupled to a surgically-prepared surface of the proximal end of a tibia. The tibial tray may include a platform and an anchor extending from the platform. The platform may include a top surface and a bottom surface. The anchor may extend downwardly from the bottom surface of the platform. The anchor may include a cavity defined therein. In such embodiments, the cavity may include an opening defined on the top surface of the platform.

The tibial insert may include a platform and a stem. The stem may extend downwardly from the platform. The stem may be configured to be received by the cavity of the tibial tray. For example, the stem may be configured to be extend below the bottom surface of the tibial tray when received in the cavity.

The opening of the cavity of the tibial tray may be generally wedge-shaped in some embodiments. In such embodiments, one end of the wedge-shaped opening may be narrower than the other end of the wedge-shaped opening. Alternatively, the opening may be oval-shaped or rectangular shaped. In some embodiments, the width of one end of the opening of the cavity of the tibial tray may be greater than the width of a corresponding end of the stem of the tibial insert. Additionally, the length of one end of the cavity of the tibial tray may be greater than the length of a corresponding end of the stem of the tibial insert. Further, in some embodiments, the longitudinal axis of the cavity of the tibial tray may be parallel to an inboard surface of the platform of the tibial tray. Alternatively, the longitudinal axis of the cavity of the tibial tray may be angled with respect to an inboard surface of the platform of the tibial tray. Additionally, in some embodiments, a bottom surface of the cavity of the tibial tray may be positioned below the bottom surface of the platform of the tibial tray.

Accordingly to a further aspect, a method for implanting a mobile tibial assembly may include securing a tibial tray to a surgically prepared surface of the proximal end of a tibia. The tibial tray may include a platform and an anchor. The platform may include a top surface and a bottom surface. The anchor may extend downwardly from the bottom surface of the platform. The anchor may include a cavity defined therein. The cavity may have an opening defined on the top surface of the platform. The method may also include inserting a stem of a unicompartmental tibial insert into the cavity of the tibial tray such that a bottom end of the stem is positioned inferiorly relative to the bottom surface of the platform.

BRIEF DESCRIPTION OF THE DRAWINGS

The detailed description particularly refers to the accompanying figures in which.

DETAILED DESCRIPTION OF THE DRAWINGS

Figure 1:
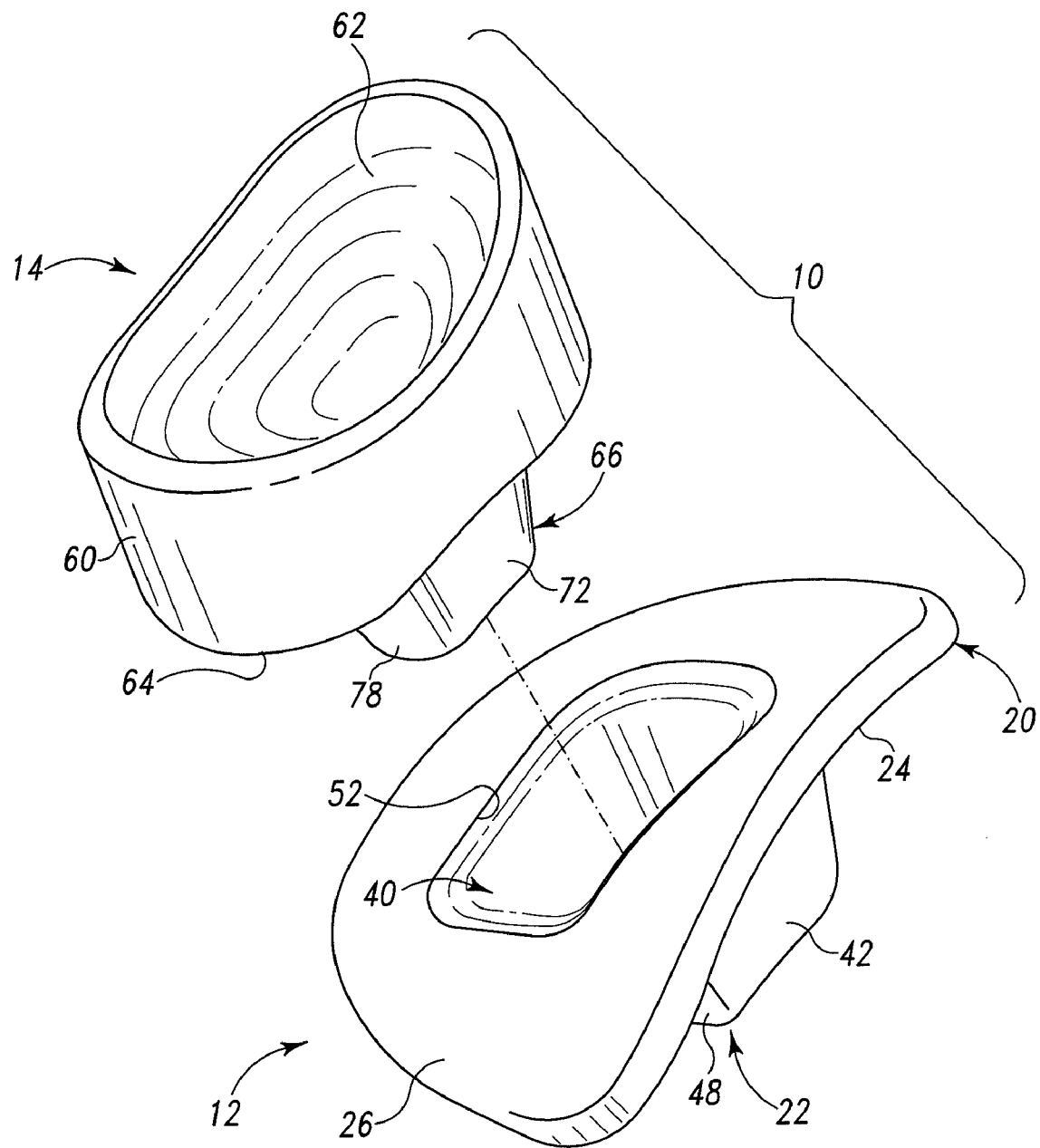
FIG. 1 is an exploded, perspective view of a unicompartmental tibial assembly.

While the concepts of the present disclosure are susceptible to various modifications and alternative forms, specific exemplary embodiments thereof have been shown by way of example in the drawings and will herein be described in detail. It should be understood, however, that there is no intent to limit the disclosure to the particular forms disclosed, but on the contrary, the intention is to cover all modifications, equivalents, and alternatives following within the spirit and scope of the invention as defined by the appended claims.

Various unicompartmental tibial assemblies are disclosed herein. Each tibial assembly includes a tibial tray configured to be secured to a surgically-prepared surface of the proximal end of a patient's tibia and a tibial insert configured to mate with the tibial tray. The tibial insert includes an upper bearing surface configured to mate with a corresponding condylar surface of a natural or prosthetic femoral condyle (not shown). Each of the tibial assemblies disclosed herein is a mobile tibial assembly such that the tibial insert of each assembly is movable relative to the tibial tray of that particular assembly. Illustratively, the motion of the tibial insert of each assembly disclosed herein is constrained in one or more directions due to the configuration of the interface between the tibial tray and the tibial insert. Illustratively, as is discussed in greater detail below in reference to each specific embodiment disclosed, each tibial insert disclosed herein includes a platform and a keel or stem extending downwardly from the platform. The stems of the tibial inserts disclosed herein, each having various designs and configurations, mate with a corresponding recess of a respective tibial tray in order to constrain the motion of the tibial insert relative to the tibial tray in a particular manner.

Figure 2:
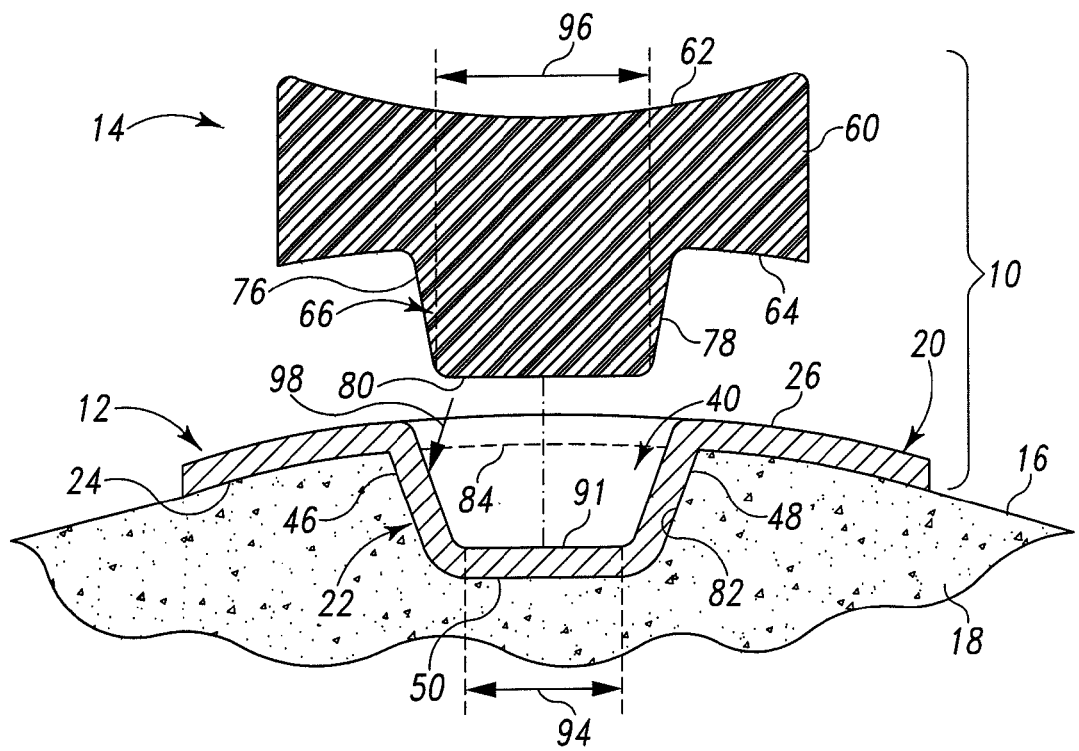
FIG. 2 is an exploded, side-sectional view of the tibial assembly of FIG. 1 showing the tibial tray coupled to a patient's tibia.
Figure 3:
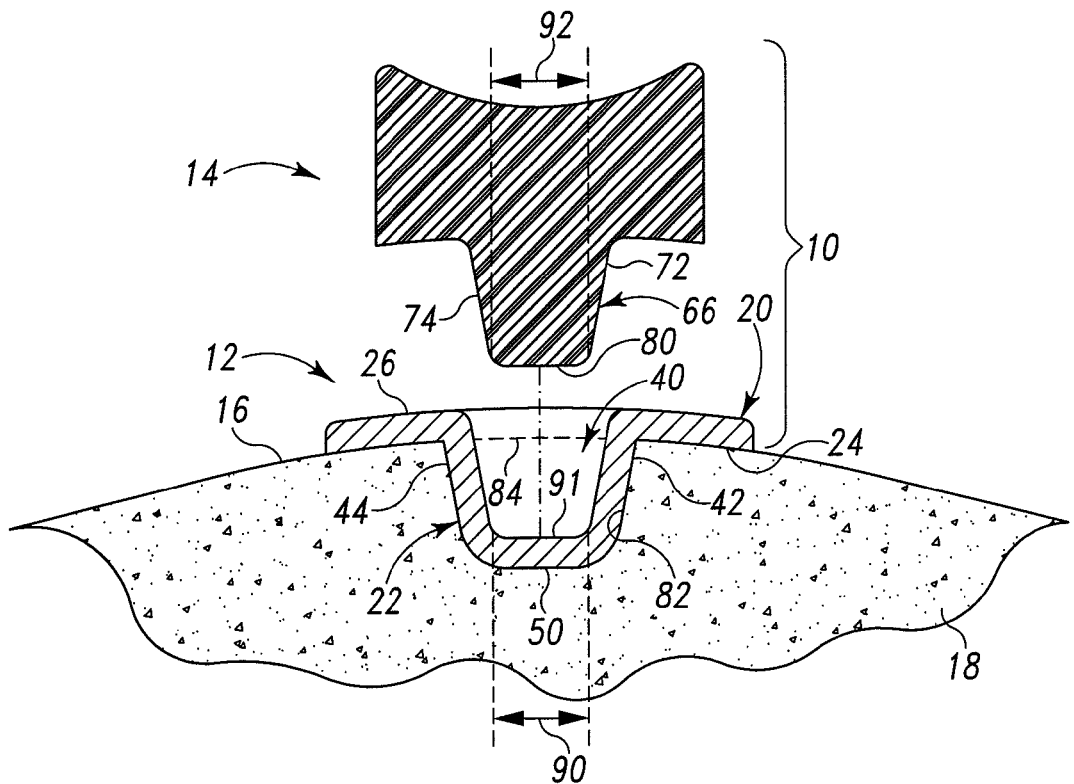
FIG. 3 is an exploded, front-sectional view of the tibial assembly of FIGS. 1-2.

Referring to FIGS. 1-6, a tibial assembly 10 includes a tibial tray 12 and a tibial insert 14 provided for use with the tibial tray 12. As shown in FIGS. 2 and 3, the tibial tray 12 is configured to be coupled to a surgically-prepared outer surface 16, having a recess 82 formed therein, of a proximal end of the patient's tibia 18. Illustratively, the assembly 10 is a unicompartmental assembly intended to replace only one of the two bearing surfaces of a tibia, for example. As such, the tibial assembly 10 may be used by a surgeon or other technician during a unicompartmental knee arthroplasty (UKA). Illustratively, the assembly 10, as well as other tibial assemblies disclosed herein, is suitable for use or implantation by surgeons adopting either conventional or minimally invasive surgical method of performing UKA. Further, although the tibial assembly 10 is a unicompartmental tibial assembly, it is within the scope of this disclosure that the various features associated with the tibial assembly 10, as well as other tibial assemblies discussed herein, may also be associated with tibial assemblies typically used during total knee arthroplasty (TKA) to replace both bearing surfaces of the tibia. Further still, it is within the scope of this disclosure for the various features associated with the many tibial assembly embodiments disclosed herein to be associated with other types of orthopaedic implants including, but not limited to, hip implants, shoulder implants, elbow implants, spine implants, finger implants, toe implants, wrist implants, and ankle implants.

Figure 4:
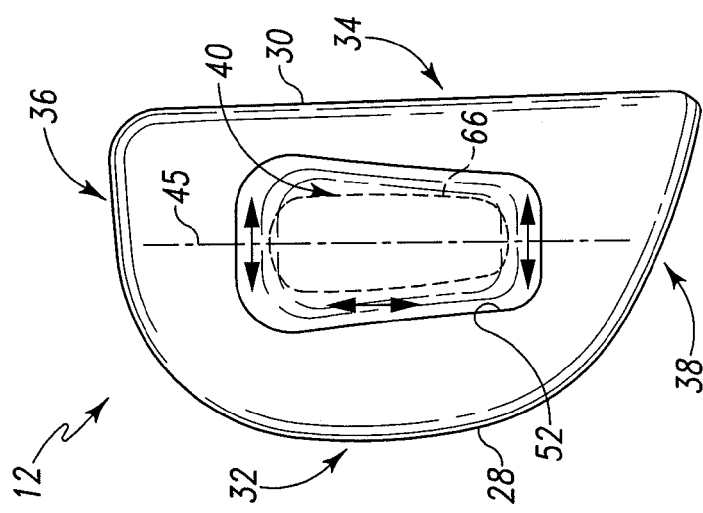
FIG. 4 is a plan view of the tibial tray of FIGS. 1-3.

Looking now to FIGS. 1-4, the tibial tray 12 includes a platform 20 and an anchor 22 extending downwardly from the platform 20. Illustratively, the anchor 22 is a single keel having four outer walls, as is described in greater detail below. During UKA, for example, the anchor 22 of the tray 12 is positioned within the patient's tibia 18, as shown in FIGS. 2 and 3, such that a bottom surface 24 of the platform 20 rests upon the surgically-prepared surface 16 of the tibia 18. Illustratively, the bottom surface 24 of the platform 20 is curved, as shown in FIGS. 1-3. However, it is within the scope of this disclosure for the bottom surface 24 of the platform 20 to be generally straight as well. The platform 20 further includes an upper surface 26 and is generally "D-shaped" when viewed in a plan view, as shown in FIG. 4, to define a curved, outer or outboard surface 28 and a generally straight inner or inboard surface 30. However, in other embodiments, the platform 20 may have other configurations based on, for example, the particular joint with which the assembly 10 is used.

Illustratively, the outboard surface 28 defines an outboard side 32 of the tibial tray 12 while the inboard surface 30 defines an inboard side 34 such that the tray 12 is further oriented to define a rear, or posterior side 36 and a front, or anterior, side 38. It should be appreciated that the illustrative tibial assembly 10 is but one embodiment of a tibial assembly and that the features and components of the tibial assembly 10 may be used with a tibial assembly configured to replace the medial and/or lateral condyle of a patient's right tibia, as well as, the medial and/or lateral condyle of the patient's left tibia.

The tibial tray 12 further includes a recess, illustratively, a cavity 40, formed through the platform 20 and into the anchor 22. In particular, the cavity 40 is defined by four outer walls of the anchor 22 (e.g., the inboard and outboard walls 42, 44 and the anterior and posterior walls 46, 48) as well as a bottom wall 50 coupled to each of the outer walls 42, 44, 46, 48, as shown in FIGS. 2 and 3. Illustratively, each of the four outer walls 42, 44, 46, 48 is angled inwardly toward each other outer wall in a direction away from the platform 20 and toward the bottom wall 50. As such, a surface area of the opening 52 of the cavity 40 formed in the upper surface 26 of the platform 20 is larger than the surface area of the bottom wall 50. Further illustratively, the opening 52 of the cavity 40 is generally wedge-shaped, as shown in FIG. 4. The posterior end 36 of the opening 52 is wider than the anterior end 36 of the opening 52. However, it is within the scope of this disclosure to include a wedge-shaped opening of the cavity having a wider anterior end and a narrower posterior end. It should further be understood that while the anchor 22 defines rounded or curved edges where adjacent walls 42, 44, 46, 48, and 50 of the anchor 22 meet, straight edges may be provided as well.

Similar to the tibial tray 12, the tibial insert 14 includes a platform 60 having an upper bearing surface 62 and a curved bottom surface 64 to rest on the curved upper surface 26 of the tray 12. A stem 66 of the insert 14 extends downwardly from the bottom surface 64 of the platform 60. Illustratively, the stem 66 includes an inboard surface 72, an outboard surface 74, a posterior surface 76, and an anterior surface 78, and a bottom surface 80 as shown in FIGS. 1 and 3.

Similar to the anchor 22 of the tibial tray 12, each of the four outer surfaces 72, 74, 76, 78 of the stem 66 are angled inwardly toward each other in a direction away from the platform 60 and toward the bottom surface 80. Accordingly, the surface area of the bottom surface 80 of the stem 66 is smaller than the surface area of portion of the stem 66 attached to the platform 60. It should be understood that the stem 66 defines rounded or curved edges where adjacent surfaces 72, 74, 76, 78, and 80 of the stem 66 meet. However, straight edges may be provided as well. Illustratively, the shape of the bottom surface 80 of the stem 66 (as well as the cross-sectional shape of the stem 66 when taken through a horizontal plane) is generally oval, as is shown in FIG. 4 and discussed in greater detail below. While the stem 66 and the platform 60 are coupled to each other to create a unitary insert 14, it is within the scope of this disclosure to provide a modular insert having separate platform and stem components which are coupled together.

The illustrative platform 60 of the tibial insert 14 is generally oval in shape when viewed in a plan view, but may define other suitable shapes as well. The illustrative upper bearing surface 62 of the platform 60 is configured to cooperate with a corresponding condylar surface of a natural or prosthetic femoral condyle. Accordingly, the bearing surface 62 provides a surface upon which the femoral component articulates relative to the tibial insert 14.

The illustrative tibial tray 12 is made of metal, such as stainless steel, cobalt chrome, or titanium, for example. The illustrative tibial insert 14, on the other hand, is made of a polymer plastic such as UHMWPE. However, it is within the scope of this disclosure for each of the tibial tray 12 and the tibial insert 14, as well as other tibial trays and inserts disclosed herein, to be made from other suitable materials as well. For example, the tibial tray 12 and/or the tibial insert 14 may be formed from a polymer material, a ceramic material, a metallic material, a bio-engineered material, or the like, in other embodiments.

In use, the tibial tray 12 is coupled to the proximal end of a patient's tibia 18, as shown in FIGS. 2 and 3, such that the bottom surface 24 of the platform 20 is engaged with and adjacent to the surgically-prepared surface 16 of the tibia 18. Illustratively, the anchor 22 is positioned within a comparably-sized opening 82 formed into the surgically-prepared outer surface 16 of the tibia 18 such that the outer and bottom walls 42, 44, 46, 48, 50 of the anchor 22 are positioned below the surgically-prepared outer surface 16 of the tibia 18. Illustratively, the surgically-prepared outer surface 16 of the tibia 18 defines an interface level, or the interface at which the platform 22 of the tibial tray 12 and the patient's tibia 18 interact or meet. The interface level is also represented in FIGS. 2 and 3 by a dotted line 84 extending across the cavity 82 formed in the tibia 18.

The stem 66 of the tibial insert 14 is received within the cavity 40 of the tibial tray 12 such that the bottom surface 64 of the platform 60 of the insert 14 is adjacent to and rests on with the upper surface 26 of the platform 22 of the tray 12. As is discussed in greater detail below, the stem 66 of the insert 14 is smaller than the cavity 40 of the tray 12 to allow the tibial insert 14 to move in a constrained manner relative to the tibial tray 12. For example, as shown in FIG. 3, the illustrative width 90 of the inside surface 91 of the bottom wall 50 of the anchor 22 of the tibial tray 12 when taken through a particular cross-sectional plane is greater than the illustrative width 92 of the bottom surface 80 of the stem 66 of the insert 14 when taken through the same cross-sectional plane. The oval shape of the stem 66 provides for a generally consistent medial/lateral width of the distal end of the stem 66 when taken along any cross-sectional plane along the anterior/posterior length of the stem 66. However, the wedge-shape of the cavity 40 provides for a decreasing medial/lateral width of the surface 91 of the cavity 40 when taken along cross-sectional planes from the posterior end of the cavity 40 to the anterior end of the cavity 40. However, the width of the anterior end 38 (or narrowest portion) of the inside surface 91 of the bottom wall 50 of the anchor 22 of the tray 12 is greater than the width 92 of the bottom surface 80 of the stem 66 of the insert 14. Looking now to FIG. 2, the illustrative length 94 of the inside surface of the bottom wall 50 of the tray 12 is greater than the illustrative length 96 of the bottom surface 80 of the insert 14. Accordingly, as shown in FIG. 4, the stem 66 of the insert 14 is able to move in within the cavity 40 of the tray 12 in anterior, posterior, medial, and lateral directions or any combination thereof. Furthermore, limited rotation of the insert 14 relative to the tray 12 is also permitted.

As noted above, a cross-sectional shape of the stem 66 of the insert is generally oval while the shape of the opening 52 of the cavity 40 is wedge-shaped. Illustratively, the width of the wedge-shaped cavity 40 is larger at the posterior end 36 of the tray 12 than at the anterior end 38 of the tray 12 and the inboard and outboard side walls 42, 44 of the anchor 22 are angled toward each other in a anterior direction. Accordingly, the posterior end of the stem 66 is able to move side-to-side (i.e., medially and laterally) more freely than the anterior end of the stem 66 is able to move relative to the tray 12. Thus, the interaction of the stem 66 within the cavity 40 operates to provide more medial-lateral movement of the stem 66 when in the posterior position and less medial-lateral movement of the stem 66 when in the anterior position (including rotational movement). In other words, the tibial insert 14 is more constrained at the anterior end and less constrained at the posterior end. It is within the scope of this disclosure, however, to provide a tibial insert which is more constrained at the posterior end of the assembly and less constrained at the anterior end of the assembly as well.

Illustratively, while the shape of the stem 66 of the tibial insert 14 is generally oval and the cavity 40 of the tray 12 is generally wedge-shaped, it is within the scope of this disclosure for the stem 66 of the tibial insert 14 to be wedge-shaped as well. Furthermore, as is discussed below, the shape of the cavity 40 of the tray 12 may be oval as well. Accordingly, it is within the scope of this disclosure to provide a tibial insert having a stem shaped the same as or differently from that of the cavity of the corresponding tibial tray. It is therefore within the scope of this disclosure to provide various tibial inserts having stems of various shapes for use with the tibial tray 12 in order to constrain movement of the tibial insert relative to the tibial tray in any suitable manner. In other words, it is within the scope of this disclosure to provide a mating recess of a tibial tray and a stem of a tibial insert being sized and configured to constrain and/or permit movement of the tibial insert relative to the tibial tray in any number of suitable ways. For example, the width of the keel of the tray and the width of the stem of the insert may be sized to generally prevent medial/lateral movement of the insert relative to the tray while the length of the keel of the tray and the length of the stem of the insert may be sized to generally permit a particular amount of anterior/posterior movement of the insert relative to the tray, or visa versa. Such configurations further operate to generally limit rotation of the insert relative to the tray as well. Further illustratively, the slope of the outer walls 42, 44, 46, 48 of the anchor 22 is generally the same as or similar to the slope of the outer surfaces 72, 74, 76, 78 of the stem 66. However, it is within the scope of this disclosure to provide a keel of an insert and a stem of a tray having corresponding outer surfaces and outer walls defining different slopes.

As noted above, the cavity 40 of the tibial tray 12 is formed through the platform 20 and into the anchor 22. Accordingly, the bottom wall 50 of the anchor 22 is positioned below the bottom surface 24 of the platform 20. As such, when the tray 12 is secured to a patient's tibia 18, at least a portion of the cavity 40 is positioned below the surgically-prepared outer surface 16 of the tibia 18.

Looking now to FIG. 2, an illustrative force component 98 of the tibial insert 14 acts on the tibial tray 12 when the tibial insert 14 and the tibial tray 12 are coupled together and implanted in a patient. The illustrative force component 98 includes the weight of the patient and the particular stresses and strains placed on the tibial tray 12 via the tibial insert 14 as provided by the particular characteristics and uses of the patient. While only the force component 98 is illustrated, various other force components similar to the force component 98 act on the tibial tray 12 during normal operation of the tibial assembly 10. Accordingly, the force component 98 is merely a representative example of the many force components acting on the tibial tray 12 via the tibial insert 14. Illustratively, because both the cavity 40 of the tray 12 and the stem 66 of the insert 14 extend below the platform 20 of the tray 12, the force component 98 acts on the tibial tray 12 at a location below the interface level 84, or below the surgically-prepared outer surface 16 of the patient's tibia 18. Therefore, any moment created by the force component 98 does not encourage lift-off of the tray 12, or upward movement of the tray 12, away from the tibia 18. In particular, force components which act on the tray 12 at a location below the interface level 84 operate to transfer the force load downwardly and into the patient's tibia 18 to maintain contact between the tray 12 and the tibia 18, to aide in fixation of the tray 12 within the tibia 18, and to help prevent lift-off of the tray 12 away from the tibia 18.

Figure 6:
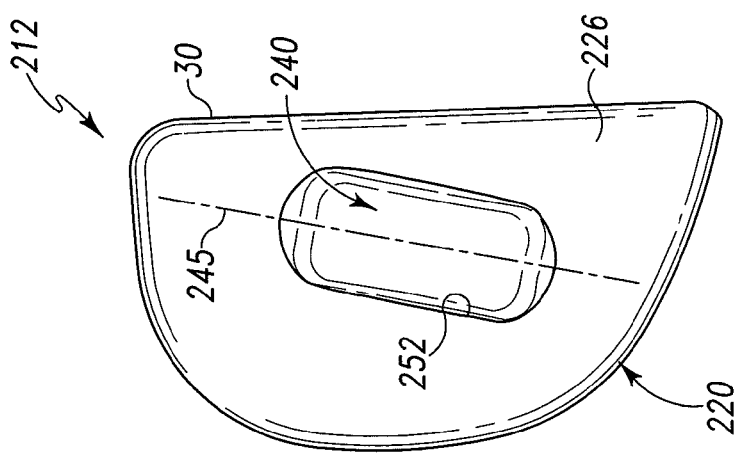
FIG. 6 is a plan view of another embodiment of the tibial tray of FIG. 4.
Figure 5:
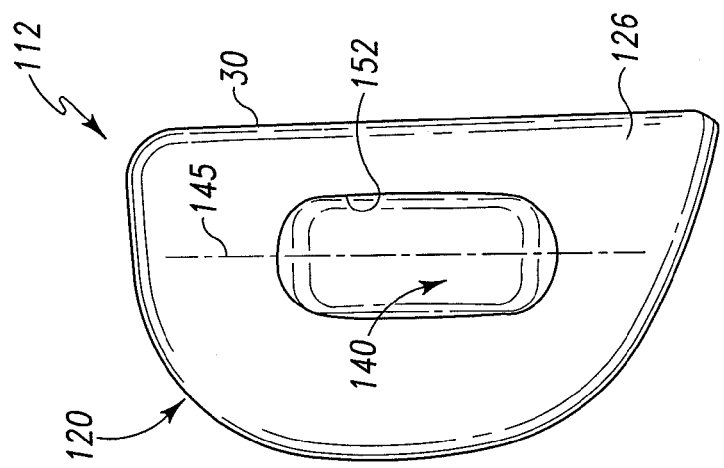
FIG. 5 is a plan view of another embodiment of the tibial tray of FIG. 4.
Figure 7:
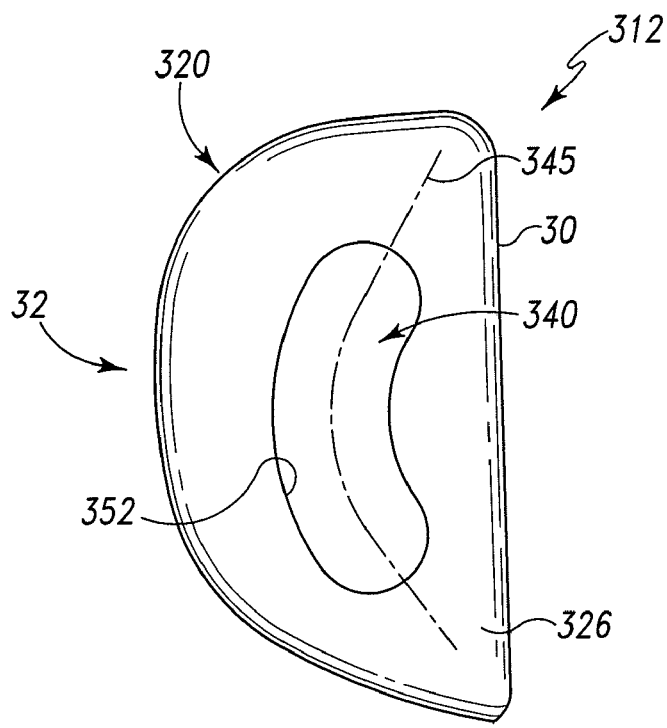
FIG. 7 is a plan view of another embodiment of the tibial tray of FIG. 4.

Looking now to FIGS. 5-7, tibial trays 112 and 212 are shown. Illustratively, the shape of the opening 152 formed in the upper surface 126 of the platform 120 of the tray 112 is oval in shape. Similarly, the shape of the opening 252 formed in the upper surface 226 of the platform 220 of the tray 212 is oval in shape as well. As with the cavity 40, the cavities 140, 240 of trays 112, 212 are each defined by angled side walls and a bottom wall. Accordingly, while wedge-shaped and oval-shaped openings of the cavities of various tibial trays are shown, it is within the scope of this disclosure to include openings of various other suitable shapes as well. For example, the opening may be square-shaped, rectangular, circular, triangular, etc.

As shown in FIG. 5, the longitudinal axis 145 of the opening 152 is generally parallel to the inboard surface 30 of the platform 120. Similarly, the longitudinal axis 45 of the generally wedge-shaped opening 52 of the tray 12 is also parallel to the inboard surface 30 of the platform 20. However, the longitudinal axis 245 of the opening 252 of the tray 212 is angled with respect to the inboard surface 30 of the platform 220, as shown in FIG. 6. Illustratively, the longitudinal axis 245 is angled toward the inboard surface 30 when moving in a posterior direction along tray 212. However, the axis 245 may be angled away from the inboard surface 30 when moving in a posterior direction along the tray 212 as well.

Alternatively, in other embodiments, a tibial tray 312 may include a platform 320 having a cavity 340 defined in an upper surface 326 as shown in FIG. 7. The cavity 340 may have a generally curved top profile shape. That is, the longitudinal axis 345 of the cavity 340 may be inwardly curving toward the inboard surface 30 as illustrated in FIG. 7. Alternatively, in other embodiments, the longitudinal axis 345 of the cavity 340 may be inwardly curving toward the outboard surface 32. Additionally, the anterior end 38 of the cavity 340 may have a width that is substantially greater than, less than, or equal to the posterior end 36. Accordingly, the longitudinal axis of the opening of any cavity provided within a tibial tray may be generally parallel to the inboard surface of the platform of that tray or may be angled with respect to the inboard surface of that tray. The longitudinal axis may further be angled relative to the inboard surface to any suitable degree and may be angled toward or away from the inboard surface in any direction.

Figure 8:
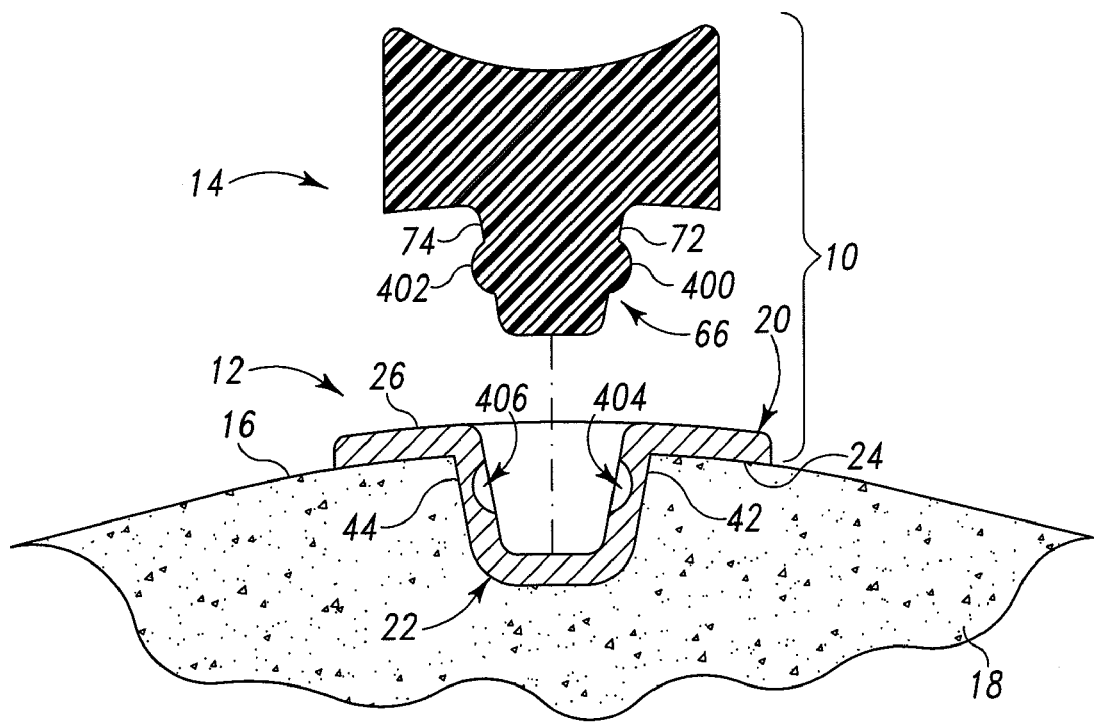
FIG. 8 is an exploded, side-sectional view of another embodiment of the unicompartmental tibial assembly of FIG. 1

In some embodiments, the stem 66 of the tibial insert 14 may include one or more protrusions. For example, as illustrated in FIG. 8, the stem 66 may include a protrusion 400 defined on and extending from the inboard surface 72 and a protrusion 402 defined on and extending from the outboard surface 74. In such embodiments, the anchor 22 of the tibial tray 12 may include a recess 404 defined in the inboard surface 42 and a recess 406 defined in the outboard surface 44. The recesses 404, 406 are configured to receive the protrusions 400, 402, respectively, when the tibial insert 14 is coupled to the tibial tray 12. That is, when the stem 66 of the tibial insert 14 is inserted into or otherwise received by the cavity 40, 140, 240, 340 of the tibial tray 12, 120, 212, 314, the protrusions 400, 402 are received in the recesses 404, 406. Once so received, the walls defining the recesses 404, 406 retrain the protrusion 400, 402 therein and reduce the likelihood that the tibial insert 12 will lift off from the tibial tray tibial tray 12, 120, 212, 314. In addition, in such embodiments, the tibial insert 12 may be free to move in the anterior-posterior and/or medial-lateral direction within the cavity 40, 140, 240, 340. For example, in one particular embodiment, the recesses 404, 406 form a track defined in the respective surfaces 72, 74 such that the stem 66 is configured to move along the track in the anterior-posterior direction.

The tibial assembly 10 disclosed herein is a mobile tibial assemblies. That is, the tibial insert of the assembly 10 is able to move relative to the tibial tray. The movement of the tibial insert relative to the corresponding tibial tray, however, is constrained, or limited, such that the tibial insert is not able to freely move in all directions relative to the tibial tray. The various mating components of the tibial assembly 10 cooperate to define the particular constrained motion of the tibial insert relative to the corresponding tibial tray. The mating components include, for example, the stem of the tibial insert (or portion of the tibial insert which extends downwardly from the platform of the tibial insert) and the corresponding recess (e.g., a cavity or channel) formed in the tibial tray. The size and configuration of each of the mating components of a particular tibial assembly cooperate to define the particular constrained motion of the tibial insert relative to the tibial tray. As discussed above, the size and configuration of each of these components may be altered in order to change or adjust the motion of the tibial insert relative to the tray in order to increase or decrease the anterior, posterior, medial, lateral and/or rotational motion of the tibial insert in a particular manner. Accordingly, it is within the scope of this disclosure to include other mobile tibial assemblies whereby the tibial tray and the tibial insert include mating components having different sizes and/or configurations than those particularly disclosed herein.

The tibial trays 12, 112, 212, as well as the tibial inserts 14 disclosed herein each include various features and/or components which may be incorporated into each other tibial tray and tibial insert disclosed herein. In other words, a number of tibial assemblies disclosed herein include a tibial tray and a tibial insert having corresponding convex and concave mating surfaces while other tibial assemblies include a tibial tray and a tibial insert having corresponding planar mating surfaces. It is within the scope of this disclosure for those tibial assemblies including a tibial tray and a tibial insert having convex and concave mating surface to include planar mating surfaces while those tibial assemblies including a tibial tray and a tibial insert having planar mating surfaces may instead include convex and concave mating surfaces as well. Similarly, other features particular to one or more tibial trays and/or tibial inserts disclosed herein may be included or interchanged with certain features of other tibial tray and tibial insert embodiments.

While the concepts of the present disclosure have been illustrated and described in detail in the drawings and foregoing description, such an illustration and description is to be considered as exemplary and not restrictive in character, it being understood that only the illustrative embodiments have been shown and described and that all changes and modifications that come within the spirit of the disclosure are desired to be protected.

There are a plurality of advantages of the concepts of the present disclosure arising from the various features of the systems described herein. It will be noted that alternative embodiments of each of the systems of the present disclosure may not include all of the features described yet still benefit from at least some of the advantages of such features. Those of ordinary skill in the art may readily devise their own implementations of a system that incorporate one or more of the features of the present disclosure and fall within the spirit and scope of the invention as defined by the appended claims.

The invention claimed is:

1. A mobile tibial assembly comprising:
a tibial tray configured to be coupled to a surgically-prepared surface of a proximal end of a tibia, the tibial tray including (i) a platform having a curved upper surface, the curved upper surface having a first substantially straight edge that defines an anterior end of a generally wedge-shaped opening in the curved upper surface and a second substantially straight edge that defines a posterior end of the wedge-shaped opening, the first substantially straight edge being shorter than the second substantially straight edge such that the anterior end of the wedge-shaped opening is narrower than the posterior end of the wedge-shaped opening, (ii) an anchor extending downwardly from a bottom surface of the platform, and (iii) a cavity extending downwardly from the generally wedge-shaped opening formed in the upper surface of the platform of the tibial tray into the anchor; and a unicompartmental tibial insert including (i) a platform having an upper bearing surface and a curved bottom surface configured to contact the curved upper surface of the platform of the tibial tray and (ii) and a stem extending downwardly from the curved bottom surface of the platform of the unicompartmental tibial insert through the generally wedge-shaped opening in the upper surface of the platform of the tibial tray, the stem being received within the cavity of the tibial tray such that a bottom surface of the stem of the unicompartmental tibial insert is positioned below a bottom surface of the platform of the tibial tray.

2. The mobile tibial assembly of claim 1, wherein
(i) the anchor of the tibial tray includes a medial wall, a lateral wall, an anterior wall, a posterior wall, and a bottom wall, and
(ii) the medial, lateral, anterior, and posterior walls each extend downwardly from the bottom surface of the platform of the tibial tray and are each angled toward each other in a direction away from the bottom surface of the tibial tray.

3. The mobile tibial assembly of claim 1, wherein a width of the opening of the cavity of the tibial tray is greater than a width of a corresponding end of the stem of the unicompartmental tibial insert.

4. The mobile tibial assembly of claim 1, wherein a length of a first end of the cavity of the tibial tray is greater than a length of a corresponding end of the stem of the unicompartmental tibial insert.

5. The mobile tibial assembly of claim 1, wherein a longitudinal axis of the cavity of the tibial tray is parallel to an inboard surface of the platform of the tibial tray.

6. The mobile tibial assembly of claim 1, wherein a longitudinal axis of the cavity of the tibial tray is angled with respect to an inboard surface of the platform of the tibial tray.

7. The mobile tibial assembly of claim 1, wherein:
(i) the stem of the unicompartmental tibial insert includes a protrusion extending from a side surface, and
(ii) the tibial tray includes a recess defined in a side wall that defines the cavity, the protrusion being received in the recess.

8. The mobile tibial assembly of claim 1, wherein the stem has a generally oval-shaped cross-section.

9. The mobile tibial assembly of claim 1, wherein the stem has a generally wedge-shaped cross-section.

10. A mobile tibial assembly comprising:
a tibial tray configured to be coupled to a surgically-prepared surface of a proximal end of a tibia, the tibial tray including (i) a platform having a curved top surface and a bottom surface, the curved top surface having a first substantially straight inner edge and a second substantially straight inner edge, the first substantially straight inner edge being shorter than the second substantially straight inner edge, and (ii) an anchor extending downwardly from the bottom surface of the platform, the anchor having a cavity defined therein, the cavity having a generally wedge-shaped opening defined on the curved top surface of the platform, the first substantially straight inner edge defining an anterior end of the wedge-shaped opening and the second substantially straight inner edge defining a posterior end of the wedge-shaped opening such that the anterior end of the wedge-shaped opening is narrower than the posterior end of the wedge-shaped opening; and
a unicompartmental tibial insert including (i) a platform having a curved bottom surface configured to contact the curved top surface of the platform of the tibial tray and (ii) a stem extending downwardly from the platform, the stem being configured to extend through the opening defined on the curved top surface of the platform of the tibial tray and be received by the cavity of the tibial tray,
wherein (i) the stem of the unicompartmental tibial insert is configured to extend below the bottom surface of the tibial tray when received in the cavity, (ii) a width of the opening of the cavity of the tibial tray is greater than a width of a corresponding end of the stem of the unicompartmental tibial insert, and (iii) a length of a first end of the cavity of the tibial tray is greater than a length of a corresponding end of the stem of the unicompartmental tibial insert.

11. The mobile tibial assembly of claim 10, wherein a longitudinal axis of the cavity of the tibial tray is parallel to an inboard surface of the platform of the tibial tray.

12. The mobile tibial assembly of claim 10, wherein a longitudinal axis of the cavity of the tibial tray is angled with respect to an inboard surface of the platform of the tibial tray.

* * * * *